United States Patent
Makerri et al.

(10) Patent No.: US 10,981,084 B2
(45) Date of Patent: Apr. 20, 2021

(54) USE OF COCONUT WATER AS EXTRACTION SOLVENT

(71) Applicants: BASF Beauty Care Solutions France SAS, Lyons (FR); Universite d'Avignon et des Pays du Vaucluse, Avignon (FR)

(72) Inventors: Caroline Makerri, Avignon (FR); Philippe Moser, Dommartemont (FR); Farid Chemat, Morteres les Avignon (FR); Sandrine Perino, Montfavet (FR)

(73) Assignees: BASF Beauty Care Solutions France SAS, Lyons (FR); Universite d'Avignon et des Pays du Vaucluse, Avignon (FR)

( * ) Notice: Subject to any disclaimer, the term of this patent is extended or adjusted under 35 U.S.C. 154(b) by 0 days.

(21) Appl. No.: 16/474,370

(22) PCT Filed: Dec. 22, 2017

(86) PCT No.: PCT/FR2017/053809
§ 371 (c)(1),
(2) Date: Jun. 27, 2019

(87) PCT Pub. No.: WO2018/122514
PCT Pub. Date: Jul. 5, 2018

(65) Prior Publication Data
US 2019/0336884 A1   Nov. 7, 2019

(30) Foreign Application Priority Data

Dec. 29, 2016 (FR) ...................................... 16 63506

(51) Int. Cl.
| | |
|---|---|
| *B01D 11/02* | (2006.01) |
| *A61K 8/97* | (2017.01) |
| *A61Q 19/00* | (2006.01) |
| *A61K 36/88* | (2006.01) |
| *A23L 33/105* | (2016.01) |
| *A61K 8/9794* | (2017.01) |

(52) U.S. Cl.
CPC ........ *B01D 11/0288* (2013.01); *A23L 33/105* (2016.08); *A61K 8/9794* (2017.08); *A61Q 19/00* (2013.01); *B01D 11/0265* (2013.01); *A61K 2236/00* (2013.01); *A61K 2800/10* (2013.01); *A61K 2800/49* (2013.01)

(58) Field of Classification Search
CPC . B01D 11/0288; B01D 11/0265; B01D 11/00; B01D 1/00; B01D 11/0261; B01D 11/0292; B01D 21/26; B01D 21/262; B01D 36/00; B01D 37/00; A61K 8/9794; A61K 2800/10; A61K 2800/49; A61K 2236/00; A61K 36/889; A61K 8/97; A61K 2800/00; A61K 2236/30; A61K 2236/31; A61K 2236/331; A61K 2236/333; A61K 2236/39; A61K 2236/50; A61K 2236/51; A61K 2236/53; A61K 2236/55; A61Q 19/00; A23L 33/105
USPC ..... 210/634, 639, 806, 748.02, 748.07, 774, 210/804; 424/520, 195.15–195.18, 725, 424/780; 554/8, 15, 23, 175
See application file for complete search history.

(56) References Cited

U.S. PATENT DOCUMENTS

| | | | | |
|---|---|---|---|---|
| 4,689,232 A | * | 8/1987 | Moeschler | A01N 65/08 424/725 |
| 5,281,732 A | * | 1/1994 | Franke | A23C 19/06 554/16 |
| 5,891,440 A | * | 4/1999 | Lansky | A61K 36/185 424/727 |
| 8,632,829 B2 | | 1/2014 | Hammerstone, Jr. et al. | |
| 10,188,083 B2 | * | 1/2019 | Leo | A01K 67/033 |
| 2004/0262221 A1 | * | 12/2004 | Herold | B01D 11/0288 210/634 |
| 2006/0039887 A1 | * | 2/2006 | Gupta | A61K 36/28 424/74 |
| 2008/0317891 A1 | | 12/2008 | Anderson et al. | |
| 2010/0022788 A1 | * | 1/2010 | Farid | G01N 1/44 554/21 |
| 2011/0123648 A1 | * | 5/2011 | Wu | A61K 36/889 424/727 |
| 2016/0122706 A1 | | 5/2016 | Riveroll et al. | |
| 2018/0071933 A1 | * | 3/2018 | Griffin | B26B 21/4081 |
| 2018/0085303 A1 | * | 3/2018 | Peterson | A61K 8/9711 |
| 2019/0085279 A1 | * | 3/2019 | Leo | A23L 2/56 |

FOREIGN PATENT DOCUMENTS

| | | |
|---|---|---|
| EP | 1913821 A1 | 4/2008 |
| EP | 1955749 B1 | 3/2010 |
| JP | 2006052191 A | 2/2006 |

OTHER PUBLICATIONS

International Search Report for PCT/FR2017/053809 dated Mar. 6, 2018 with English translation Attached.
Written Opinion of the International Searching Authority for PCT/FR2017/053809 dated Mar. 6, 2018 (in French).

* cited by examiner

*Primary Examiner* — Joseph W Drodge
(74) *Attorney, Agent, or Firm* — Faegre Drinker Biddle & Reath LLP

(57) ABSTRACT

The present invention relates to the use of coconut water as extraction solvent, to extraction methods using coconut water and extracts obtained by extraction with coconut water.

20 Claims, No Drawings

USE OF COCONUT WATER AS EXTRACTION SOLVENT

RELATED APPLICATIONS

This application is a national stage application (under 35 U.S.C. § 371) of PCT/FR2017/053809, filed Dec. 22, 2017, which claims benefit of French Application No. 16 63506, filed Dec. 29, 2016.

FIELD OF THE INVENTION

The present invention relates to a novel solvent for natural extraction of plant origin, and to the use thereof for the extraction of natural raw materials, especially of plant origin.

TECHNOLOGICAL BACKGROUND OF THE INVENTION

Organic solvents are widely used in the chemical, food, pharmaceutical and cosmetics industries for the extraction from plant raw materials of active principles or of molecules (total extracts, flavorings, fragrances, dyes, primary or secondary metabolites). Depending on the nature of the compounds targeted, solvents such as alcohols, hexane and ethyl acetate are generally used in these extraction processes. However, these solvents may be toxic, flammable, explosive or sparingly biodegradable.

Increasingly numerous and strict regulations concerning the standards for the emission of atmospheric pollutants (volatile organic compounds or the like), human health (substances classified as carcinogenic, mutagenic or reprotoxic) or the environment impose in the long term their replacement with new alternative biodegradable and sparingly toxic solvents, and which may have a broad capacity for solubilization in terms of selectivity and polarity.

Replacing petrochemistry-derived solvents has thus been a major challenge in recent decades. However, at the present time, few candidates make it possible to achieve the low production costs and high yields obtained with conventional solvents. Added to this are the regulatory constraints imposed for the registration of new chemical substances.

To overcome this problem, the use of natural substances remains the best alternative, and bio-inspired research thus appears essential.

Several types of solvents, including ionic liquids (ILs) and deep eutectic solvents (DESs), have been suggested as alternative solutions for replacing volatile organic solvents.

The term "ionic liquids" (ILs) appeared for the first time in the 1950s. Since then, research on solvents of this type has increased exponentially. Specifically, this keen interest is due to the noteworthy properties of ILs, which make them much more attractive than conventional organic solvents. Besides their high thermal stability, they have a low vapor pressure, are non-flammable and electrochemically stable. The commonly accepted definition of an IL is that it is an ionic fluid derived from a molten salt whose temperature is below or close to 100° C. (Moutiers G, Isabelle Billard. Les liquides ioniques: des solvants pour l'industrie [Ionic liquids: solvents for industry], Techniques de l'Ingénieur. January 2005, AF 6 712,1-18).

Historically, the first ILs were chloroaluminates composed of aluminum chloride and alkaline chlorides. An example of ILs of this type is $AlCl_3$—NaCl, the melting point of which is 107° C. Other generations of ILs followed, but it is the use of chloroaluminates associated with imidazolium cations which demonstrated the advantage of these media as solvents and catalysts.

Used mainly for organic synthesis, it was not until later that ILs were used as extraction solvents. While, to date, tens of thousands of publications relating to ILs have been recorded, only a few hundred relate to the extraction of natural products.

Although ILs have advantageous properties, they cannot, however, be considered as true "green" solvents. The reason for this is that their manufacturing cost and their poor biodegradability, inter alia, make them poor candidates.

Deep eutectic solvents (DESs) constitute a sub-category of ionic liquids. DESs are mixtures of at least two species that associate together via non-covalent intermolecular bonds. These interactions lead to an energy decrease characterized by the melting point of the mixture. The term "eutectic mixture" is used when the melting point, or eutectic point, of said mixture is below that of the two compounds of the mixture taken individually (Deep Eutectic Solvents (DESs) and Their Applications. Smith E L, Abbott A P, Ryder K S. Chem. Rev. 2014, 114, 11060-11082).

The synthesis of DESs takes place by complexation of a quaternary ammonium salt with a metal salt or a hydrogen-donating species. The charge delocalization takes place, for example, between a halide ion and the hydrogen-donating species, thus resulting in a reduction of the melting point of the mixture.

The properties of DESs are virtually identical to those of ionic liquids, their advantages being their ease of preparation, which is due, inter alia, to the low cost of their compound. Among these is choline chloride, which is the compound most frequently cited in the literature in the formation of DESs. Choline chloride makes it possible to form a eutectic mixture with the majority of hydrogen-donating compounds. The first eutectic system containing it was formed with urea.

Starting from this model, numerous eutectic mixture systems have been brought to light. Added to these are DESs involving other $Cat^+X^-$ mixtures. The family of betaines has thus been particularly studied for this application. Although the formation of DESs can be achieved with the latter, mixtures with choline chloride show better results, whether as regards the ease of preparation of the solvent or the yields for the extraction of molecules of interest.

Nam et al. (Green Chem., 2015, 17, 1718-1727) studied several DES systems for the plant extraction of quercetin and kaempferol. Choline chloride associated with an alcohol (glycerol, xylitol) or a sugar (glucose) were tested in comparison with other systems such as a mixture of betaine with a carboxylic acid (malic acid). The results of this study show that extraction with a DES of choline chloride/xylitol type makes it possible to obtain on average a concentration four times greater than extraction with water.

However, it should be noted that the viscosity of these DES solvents remains a problem for plant extraction. Specifically, certain systems require the addition of an additive such as water in order to be used. Added to this is the fact that the non-toxicity of DESs has not yet been demonstrated. Since the biodegradability problems of ILs were not revealed until several years after their first uses, complementary studies must be performed on DESs before they can be considered as eco-solvents.

The team of Prof. Verpoorte at the University of Leiden introduced the term "natural deep eutectic solvents" (Na-DESs) in 2011. This refers to eutectic mixtures composed solely of "natural" molecules, i.e. molecules that are found in plant cells.

However, an ongoing need for natural extraction solvents remains.

SUMMARY OF THE INVENTION

The present invention relates to the use of coconut water as a solvent for the extraction of compounds, in particular for the preparation of active principles, preferably of cosmetic active principles. The use of this natural liquid makes it possible to increase the efficiency of extraction of certain molecules, especially when compared with simple aqueous extraction.

Thus, the present invention relates to a use of coconut water as an extraction solvent, in particular for the extraction of compounds or for the preparation of extracts from plant, animal and/or prokaryotic biological material.

The present invention also relates to a method for the extraction of compounds or for the preparation of extracts from plant, animal and/or prokaryotic biological material, comprising the incubation of said plant, animal and/or prokaryotic biological material with coconut water, and the recovery of the compounds or of the extract. Preferably, the method comprises a step of immersing the biological material in coconut water; a step of extracting the mixture obtained; and a step of recovering the compounds or the extract comprising a step of centrifugation and/or filtration and/or evaporation and/or concentration and/or fractionation and/or purification or a combination of these steps. In particular, the coconut water and the biological material are used in a weight ratio of between 2:1 and 100:1, preferably between 1:1 and 100:1 or between 5:1 and 20:1, for example in a ratio of 10:1.

Optionally, an anionic, cationic or nonionic surfactant may be added to the coconut water to facilitate the extraction of the compounds.

Optionally, the extraction step may be assisted by microwaves or by ultrasound.

In a first embodiment, the extraction step is performed at a temperature of between 2° C. and 100° C., preferably between 20° C. and 90° C., for example between 50° C. and 80° C. for 15 minutes to 2 days, preferably for 30 minutes to 1 day, and in particular for 1 to 3 hours.

In another embodiment, the extraction step is performed under subcritical conditions. In particular, the extraction is performed under nitrogen and under pressures at temperatures of between 100 and 140° C. for 5 minutes to 1 hour.

Preferably, the biological material may be a plant or one or more parts thereof.

Preferably, the extracted compounds include terpenes, terpenoids, flavones and flavonoids, steroids, sterols, saponins and sapogenins, alkanes, alkaloids, amines, amino acids, aldehydes, iridoids, phenylpropanoids, alcohols, polyols, lipids, fatty acids, lignans, phenols, pyrones, butenolides, lactones, chalcones, ketones, benzenes, cyclohexanes, glucosides, glycosides, cyanidines, furans, phorbols, quinones and phloroglucinols in aglycone form or, where appropriate, in glycosyl form. The invention may also be applied to the extraction of bioactive molecules of high molecular mass such as proteins, peptides, enzymes, polysaccharides, oligosaccharides and carbohydrates.

Finally, the present invention relates to an extract of plant, animal and/or prokaryotic biological material obtained via the method according to the present invention comprising a coconut water, and also to the use of this extract for the manufacture of a nutraceutical composition, a dietetic or dietary product, a nutritional supplement, a pharmaceutical composition, notably a dermatological composition, or a cosmetic composition or to a nutraceutical, dietetic, dietary, nutritional, pharmaceutical, notably dermatological, or cosmetic composition comprising this extract. The invention also relates to a method for preparing a nutraceutical, dietetic, dietary, nutritional, pharmaceutical, notably dermatological, or cosmetic composition, comprising the preparation of an extract of plant, animal and/or prokaryotic biological material according to the method as claimed in any one of claims 2-11 and the incorporation of the extract into a nutraceutical, dietetic, dietary, nutritional, pharmaceutical, notably dermatological, or cosmetic composition.

DETAILED DESCRIPTION OF THE INVENTION

The present invention relates to the use of coconut water as an extraction solvent.

Coconut Water

The terms "coconut water" and "coconut juice" may be used equivalently in the present patent application.

The coconut tree is a monocot plant of the Arecaceae family. It forms part of the *Cocos* genus, of which there is only one species, *Cocos nucifera* L.

The species contains a large number of ecotypes or cultivars which have varied morphologies and colorings. A distinction is generally made among the varieties known as "Tall Coconut" which can grow up to 20-25 m in height and "Dwarf Coconut" varieties which rarely exceed 12 meters in height: a third category contains hybrids of these two varieties. Thus, the coconut water may come equally from a tall coconut variety, from a dwarf coconut variety or, finally, from the hybrids.

The growing of coconut trees is widespread in the subtropics. More than 80% of the surfaces planted with coconut trees are located in Asia (India, the Philippines, Indonesia, Sri Lanka and Thailand). The rest are spread between Africa, Latin America, Oceania and the West Indies.

The fruit of *Cocos nucifera* L. is a drupe of ovoid or elliptical shape, composed of a smooth epidermis of variable color, a fibrous mesocarp (or coir) and a hard, dark brown lignified endocarp (or shell) containing a kernel which corresponds to the albumen of the seed. The kernel is hollow and its central cavity contains a sterile liquid known as "coconut water" intended to enable it to germinate irrespective of the external conditions.

Commercialized coconut thus corresponds to the core of the fruit. The kernel of the mature nut is consumed as is or transformed to give coconut oil, coconut milk or coconut powder used in pastry-making.

Thus, the term "coconut water" denotes the liquid contained in the central cavity of the coconut.

The coconut fruit reaches full maturity between 11 and 12 months after fertilization. At 5 months, the kernel begins to form a thin layer of jelly around the inside of the endocarp. During the maturation process, the kernel gradually grows and replaces the coconut water with fat storage cells. At full maturity, the coconut water represents between 15% and 30% of the weight of the nut, the amount which may be harvested from each nut being about 300 ml, but depending notably on the coconut variety. The composition of coconut water changes gradually in the course of maturation.

In a first embodiment, the coconut water is a coconut water from the fruit at maturity, i.e. a fruit harvested between 11 and 12 months. In another preferred embodiment, the coconut water is a coconut water obtained from a green fruit. For example, the coconut water is collected from a nut at 5 to 11 months of maturity, for example at 5, 6, 7, 8, 9 or 10 months of maturity, preferably at 6, 7, 8 or 9 months of maturity.

In one embodiment, the coconut water comprises between 2 and 7 g of solids/100 ml.

In one embodiment, the coconut water comprises between 1.5 and 7 g of sugars/100 ml, of which between 0.5 and 5 g of reducing sugars/100 ml. Preferably, the coconut water comprises between 4 and 6 g of sugars/100 ml, of which between 2 and 4 g of reducing sugars/100 ml.

In one embodiment, the coconut water comprises between 0.75 and 2.5 g of amino acids/100 ml, preferably between 1 and 2 g/100 ml.

In one embodiment, the coconut water has an acidity of between 0.5 and 2 meq/100 ml, preferably between 0.7 and 1 meq/100 ml.

Thus, in a particular embodiment, the coconut water is characterized by the combination of two, three or four characteristics from among the following:
- between 2 and 7 g of solids/100 ml;
- between 1.5 and 7 g of sugars/100 ml, of which preferably between 1 and 5 g of reducing sugars/100 ml;
- between 0.75 and 2.5 g of amino acids/100 ml; and
- an acidity of between 0.5 and 2 meq/100 ml, preferably between 0.7 and 1 meq/100 ml.

Preferably, the sugars are chosen from sucrose, glucose, fructose, galactose, xylose and mannose.

Coconut water also comprises amino acids.

Nowadays, coconut water is a refreshing tropical drink, the international market of which is in full boom. It is also described as a "rehydrating drink for sportspeople". Consequently, many sources of coconut water are commercially available.

Extraction Processes or Methods

The present invention relates to the use of coconut water as an extraction solvent, in particular for the extraction of substances from plant and/or animal and/or prokaryotic biological material.

The invention also relates to a process or method for the extraction of compounds or for the preparation of extracts from plant, animal and/or prokaryotic biological material, comprising the placing of said plant, animal and/or prokaryotic biological material in contact with coconut water, and the recovery of the compounds or of the extract. The extraction processes are well known to those skilled in the art.

More particularly, the process may comprise a step of immersing the biological material in coconut water; a step of extraction, with or without stirring, for instance maceration or decoction or percolation or infusion of the mixture obtained; optionally, a step of centrifugation and/or filtration and/or evaporation and/or concentration and/or fractionation and/or purification or a combination of these steps.

In one particular embodiment, an anionic, cationic or nonionic surfactant may be added to the coconut water to facilitate the extraction of the target compounds.

During the step of placing in contact or immersion, the coconut water and the biological material are used in a weight ratio of between 2:1 and 100:1, preferably between 1:1 and 100:1 or between 5:1 and 20:1, for example in a ratio of 10:1.

The process may comprise a step of adjusting the extraction pH, which may be between 3 and 10. The pH of the final extract may then be adjusted, where appropriate, to a pH close to neutrality.

The temperature conditions for the step of maceration or percolation or infusion of the mixture are adapted according to the starting biological material and the substance to be extracted or the extract to be prepared.

For example, the temperature may be between 2° C. and 100° C., preferably between 20° C. and 90° C., for example between 50° C. and 80° C.

The duration of the maceration or percolation or infusion step is also to be adapted according to the starting biological material and the substance to be extracted or the extract to be prepared. The duration also depends on the extraction method performed.

For example, the duration may be between 15 minutes and 2 days, preferably between 30 minutes and 1 day, and in particular between 1 hour and 3 hours. Thus, the duration may be 30 minutes, 1 hour, 2 hours or 3 hours.

The extraction step may be performed with or without stirring, with or without sonication, optionally under irradiation (infrared, microwave), under pressure or under atmospheric conditions. Thus, the extraction step may be assisted by microwaves or by ultrasound.

Preferably, the extraction is performed under atmospheric conditions.

However, the coconut water may also be used in subcritical water extraction techniques. The extraction is performed in a high-performance microwave reactor. This extraction is preferably performed under nitrogen and under pressure, for example at 30 bar. The extraction may be performed, for example, at temperatures of between 100 and 140° C., preferably between 105° C. and 130° C., and for 5 minutes to 1 hour, preferably between 10 minutes and 30 minutes.

The extraction may be performed in one or more runs. Preferably, the extraction is performed in a single run.

The process results in the preparation of an extract of biological material. The extract obtained via the process constitutes one of the subjects of the present invention.

However, the process may comprise one or more subsequent steps for purifying a substance contained in the extract of biological material. Alternatively, the extract of biological material may be used directly for the manufacture of a nutraceutical composition, of a dietetic or dietary product, of a nutritional supplement, of a pharmaceutical composition, notably a dermatological composition, or of a cosmetic composition, without a purification step.

In particular, according to a particularly advantageous embodiment, the process does not comprise the addition of an organic solvent.

Plant, Animal and/or Prokaryotic Biological Material

Coconut water is thus useful for extracting compounds or for preparing extracts from plant and/or animal and/or prokaryotic biological material. The plant material may be terrestrial or aquatic.

For example, the biological material may be a plant or one or more parts thereof; an animal or one or more parts thereof; an alga, a lichen, a fungus, a yeast, a mold or a bacterium. For example, the plant part(s) may be chosen from the wood, the roots, the rhizome, the bark, the flowers, the petals, the sepals, the seeds, the fruits, the aerial parts, in particular the stalk, the leaves. The plant material used may or may not be differentiated (cats, plant stem cells).

The biological material may undergo treatments prior to the extraction. The biological material may be dried beforehand. For example, the biological material may be ground, chopped or the like. Milling may be performed using a ball mill, milling with a mortar, ultrasound milling, milling using a mixer, etc.

For example, the biological material may be chosen from the following nonexhaustive list:

*Agave atrovirens, Malpighia emarginata, Aucoumea klaineana, Cladosiphon okamuranus, Macadamia ternifolia, Callitris introtropica, Illicium verum, Orbignya oleifera,* babassu, Haberlea rhodopensis, Morinda officinalis, Ilex paraguariensis, Borojoa patinoi, Pichia, Berthalletia excelsa, Ptychopetalum olacoides, Paullinia cupana, Caryocar brasiliense, Copernicia cerifera, Dolichos lablab, Trifolium repens, Limnanthes alba, Meadowfoam estolide, Syringo oblata affinis, Amomum kravanh, Angelica polymorpha, Viscum album, Lithospermum officinale, Rhinacanthus communis, Lilium candidum, Patrinia villosa, Anthemis nobilis, Peucedanum praeruptorum, Hedyotis diffusa, Oldenlandia diffusa, Mucuna birdiana, Betula alba, Bletilla striata, Plumeria alba, Beauveria bassiana, Fraxinus chinensis, Michelia alba, Pyrus bretschneideri, Quercus alba, Ampelopsis japonica, Salix alba, Hydrastis canadensis, Imperata cylindrica, Aquilaria sinensis, Inula cappa, Melaleuca Leucadendra, Cynanchum stauntonii, Atractyloides macrocephala, Nymphaea alba, Tuber magnatum, Perilla frutescens, Pulsatilla chinensis, Cynanchum atratum, Dictamnus dasycarpus, Helichrysum angustifolium, Lupinus albus, Iris pallida, Lilium brownii, Centaurium erythraea, Thymus serpyllum mongolicus, Lotus corniculatus, Rosa centifolia, Fagraea berteroana, Platycladus orientalis, Orchis maculata, Geranium maculatum, Tabebuia impetiginosa, Scutellaria barbata, Cyathea cumingii, Brassica oleracea gemmifera, Mentha arvensis, Mentha haplocalix, Artemisia vulgaris, Atractyloides chinensis, Laminaria hyperborea, Cedrus atlantica, Liriodendron tulipifera, Sequoia sempervirens, Hamamelis virginiana, Pinus strobus, Juniperus virginiana, Schizandra chinensis, Scrophularia buergeriana, Hovenia dulcis, Leptospermum petersonii, Ficus pumila, Cupressus funebris, Dolichos lablab, Prinsepia utilis, Enteromorpha compressa, Astragalus complanatus, Citrus depressa peel, Polygonum aviculare, Vanilla planifolia, Iris versicolor, Angelica keiskei, Cakile maritima, Eryngium maritimum, Artemisia scoparia, Cetraria islandica, Lens esculenta, Agaricus blazeii, Peumus boldus, Rheum undulatum, Borago officinalis, Spinacia oleracea, Ananas sativus, Sclerocarya birrea, Spirulina platensis, Haematoxylon campechianum, Phaseolus vulgaris, Elaphe carinata, Cynara scolymus, Pheretima aspergillum, Echinacea pallida, Xanthium sibiricum, Atractyloides lancea, Acorus calamus, Crocus sativus, Avena strigosa, Alpinia katsumadai, Amomum tsao-ko, Hedychium spicatum, Salicornia herbacea, Fragaria ananassa, Saxifraga sarmentosa, Arbutus unedo, Gossypium herbaceum, Melilotus officinalis, Sarcandra glabra, Biota orientalis, Platycladus orientalis, Thuja orientalis, Baccharis genistelloides, Jania rubens, Camellia sinensis, Aphloia theiformis, Bupleurum chinensis, Acorus calamus, Hedera nepalensis sinensis, Pulsatilla koreana, Angelica gigas, Epimedium koreanum, Plantago asiatica, Echium plantagineum, Aquilaria agallocha, Tamarix chinensis, Corydalis turtschaninovii, Boswellia serrata, Nymphaea lotus, Fucus serratus, Phaseolus angularis, Ganoderma neo-japonicum, Pinus densiflora, Phaseolus calcaratus, Ganoderma lucidum, Cassia alata, Passiflora alata, Ailanthus altissima, Lactuca virosa, Bellis perennis, Paeonia veitchii, Codonopsis tangshen, Coix lacryma-jobi ma-yuen, Phellodendron chinense, Zanthoxylum piasezkii, Vladimiria souliei, Cyathula officinalis, Ligusticum chuanxiong, Dipsacus asper, Andrographis paniculata, Sedum sarmentosum, Betula pendula, Ulmus davidiana, Brasenia schreberi, Mentha pulegium, Argania spinosa, Juniperus formosana, Asparagopsis armata, Robinia pseudoacacia, Rosa roxburghii, Actinidia Chinensis sitosa, Capparis spinosa, Codium fragile, Sterculia urens, Acanthopanax senticosus, Eleutherococcus senticosus, Caesalpinia spinosa, Cnicus benedictus, Mitracorpus scaber, Hydrangea serrata, Plantago major, Alpinia galanga, Passiflora quadrangularis, Vaccinium macrocarpon, Citrus tangerine, Rhodiola crenulata, Theobroma grandiflorum, Portulaca grandiflora, Sesbania grandiflora, Cereus grandiflorus, Rosa odorata gigantea, Lagerstroemia speciosa, Cirsium japonicum, Grindelia robusta, Musa sapientum, Pentaclethra macroloba, Cannabis sativa, Hibiscus cannabinus, Hordeum vulgare, Cimicifuga heracleifolia, Allium sativum, Sinocalomus beecheyanus pubescens, Sargentodoxa cuneata, Plantago lanceolata, Uncaria macrophylla, Sargassum pallidum, Zostera marina, Buddleja davidii, Zizyphus jujuba, Artemisia sieversiana, Anigozanthos flavidus, Salvia miltiorrhiza, Cimicifuga simplex, Vitex trifolia simplicifolia, Crataegus monogina, Lessonia nigrescens, Lophotherum gracile, Angelica sinensis, Codonopsis pilosula, Canavalia gladiota, Cardiospermum halicacabum, Garcinia mangostana, Oryza sativa, Iris germonica, Cornus controversa, Celastrus paniculata, Thamnolia vermicularis, Kochia scoparia, Lycium chinense, Ficus tikoua, Rehmannia glutinoso, Voandzeia subterranea, lichen, Poterium sanguisorba, Sanguisorba officinalis, Cupressus sempervirens, Polygonatum kingianum, Daphne feddei, Camellia reticulata, Selaginella pulvinata, Clitoria ternatea, Eugenia caryophyllus, Taxus cuspidata, Viola mandshurica, Angelica acutiloba, Typha orientalis, Aloe perryi, Prunus yedoensis, Cordyceps sinensis mycelium, Benincasa cerifera, Benincasa hispido, Malva verticillata, Origanum heracleoticum, Berberis aquifolium, Nasturtium officinale, Pachyrrhizus erosus, Angelica pubescens, Vaccinium uliginosum, Eucommia ulmoides, Lomium album, Yucca brevifolia, Ona tuberosa, Sargassum muticum, Cassia obtusifolia, Polygonatum multiflorum, Haslea ostrearia, Ormenis multicaulis, Tupidanthus calyptratus, Eysenhardtia polystachya, Anthriscus sylvestris, Centipeda minima, Potentilla anserina, Persea gratissima, Acacia catechu, Uncaria gambir, Cynamchum auriculatum, zymomonas ferment, Terminalia ferdinandiana, Helichrysum stoechas, Rosa gallica, Lavandula stoechas, Crocus sativus, Anono squamosa, Carica papaya, Lycopersicon esculentum, Solanum lycopersicum, Psidium guajava, Cassia senna, Stellaria media, Ledebouriella divaricata, Saposhnikovia divaricata, Lilium candidum, Kigelia africana, Aframomum melegueta, Prunus africana, Khaya senegalensis, Saponaria officinalis, Torreya grandis, Dioscorea hypoglauca, Stephania tetrandra, Passiflora incarnata, Padina pavonica, Clinopodium chinense, Hyacinthus orientalis, honey, royal jelly, Pteris multifida, Impatiens balsamina, Yucca vera, Citrus medico sarcodactylis, Sechium edule, Epilobium fleischeri, Poria cocas, Spirodela polyrrhiza, Chlorella emersonii, Tetraselmis suecica, Plankton, Pinus radiata, Citrus tangerina, Rubus chingii, Rubus idaeus, Glycyrrhiza uralensis, Pueraria thomsonii, Chrysanthemum boreale, Dendranthema lavandulifolium, Origanum majorana, Ipomoea batatas, Nardostachys chinensis, Saccharum officinarum, citrus Nobilis ponki, Citrus reticulata, Canarium album, Polygonum perfoliatum, Alpinia officinarum, Scutellaria alpina, Leontopodium alpinum, Rhododendron ferrugineum, Linum alpinum, Ligusticum sinense, Pueraria lobata, Carum carvi, Actinidia polygama, rhizobian, Pelvetia canaliculata, Hypnea musciformis, Cibotium barometz, Rosa canina, Ilex cornuta, Poncirus trifoliata, Lycium chinense, Broussonetia papyrifera, Copaifera officinalis resin, Cryptolepis buchananii, Ferula galbaniflua, Eriocaulon buergarianum, Polygala japonica, Atractyloides japonica, Hypericum perforatum, Cyrtomium fortunei, Glycyrrhiza glabra, Anogeissus leiocarpus, Malpighia glabra, Usnea barbata glabrescens, Cola nitida, Chaenomeles sinensis, Pogostemon cablin, Desmodium styracifolium, Dioscoreae persimilis, Curcuma kwangsiensis, Citrus nobilis, Choerospondias axillaris, Osmanthus fragrans, Phyllostachis bambusoides, Entada phaseoloides, Vernonia cumingiana, Pinus pinaster, Morinda citrifolia, Laminaria japonica, Crambe maritima, Adenanthera pavonina, Crithmum maritimum, Lygodium japonicum, Amomum longiligulare, Pancratium maritimum, Ximenia americana, Calophyllum inophyllum, Cladosiphon novae-caledoniae, Phoenix dactylifera, Davallia mariesii, Anastatica hierochuntica, Cassia mimosoides, Tropaeolum majus, Apium graveolens, Aloe ferox, Terminalia chebula, Albizia julibrissin, Polygonum multiflorum, Magnolia grandiflora, Phyllacantha fibrosa, Tuber melanosporum, Ribes nigrum, Juglans nigra, Kadsura coccinea, Ganoderma atrum, Salix nigra, Secale cereale, Rubus fruticosus, Morus nigra, Populus nigra, Prunus serotina, Diospyros lotus, Sesamum indicum, Trifolium pratense, Ribes rubrum, Alpinia galanga, Coccinia indica, Eugenia uniflora, Carthamus tinctorius, Chrysanthemum coccineum, Pyrola incarnata, Acer rubrum, Plumeria rubra, Rhodiola rosea, Narcissus poeticus, Ononis spinosa, Nephelium lappaceum, Oxycoccus palustris, Bixa orellana, Spergularia rubra, Zingiber zerumbet, Pinus koraiensis, Lonicera hypoglauca, Freesia armstrongii, Malpighia punicifolia, Delesseria sanguinea, Adansonia digitata, Magnolia officinalis, Eriodictyon crassifolium, Bergenia crassifolia, Picrorhiza scraphulariflora, Piper nigrum, Triganella foenum-graecum, Daucus carota sativa, Juglans regia, Juglans mandshurica, Lespedeza bicolor, Cucurbitaceae, Viscum coloratura, Drynaria fortunei, Phalaenopsis amabilis, Dendrobium phalaenopsis, Saxifraga stolonifera, Cymbidium grandiflorum, Polygonum cuspidatum, Melaleuca alternifolia, Fraxinus ornus, pollen, Zanthoxylum bungeanum, Pterocarpus marsupium, Arachis hypogaea, Brassica oleracea botrytis, Rubus chingii, Uncaria sinensis, Taraxacum sinicum, Alpinia chinensis, Fuscoporia obliqua sclerotium, Inonotus obliquus, Sophora japonica, Dendrobium loddigesii, Phellodendron amurense, Dendrobium chrysanthum, Cucumis sativus, Mortierella, Patrinia scabiosoefolia, Fritillaria verticillata bulb, Artemisia annua, Primula veris, Clintonia borealis, Peucedanum graveolens, Vitex negundo, Hibiscus abelmoschus, Michelia champaco, Coptis chinensis stalk, Gentiana lutea, Phellodendron chinense, Astragalosides, Engelhardtia chrysolepis, Scutellaria baicalensis, Dioscorea panthaica, Narcissus pseudo-narcissus, Boerhavia diffusa, Lupinus luteus, Heteropanax fragrans, Smilax aristolochiaefolia, Cistus incanus, Vladimiria souliei cinerea, Tephrosia purpurea, Grifola frondosa, Pimpinella anisum, Foeniculum vulgare, Anetholea anisata, Glechoma longituba, Kniphofia uvaria, Pyracantha fortuneana, Cannabis sativa, Gnaphalium leontopodium, Simmondsia chinensis, Agastache rugosa, Ageratum conyzoides, Passiflora edulis, Abrux cantoniensis, Celosia cristata, Cinchona succirubra, Morus bombycis, Paederia scandens, Polygonaturn sibiricum, Spatholobus suberectus, Kummerowia striata, Acer palmaturn, Centella asiatica, Larrea divaricata, Spirulina maxima, Chlorella minutissima, Angelica tenuissima, Tribulus terrestris, Bulnesia sarmientoi, Panicum miliaceum, Cirsium, Irvingia gabonensis, Lepidium sativum, Ulmus campestris, Hibiscus militaris, Tasmannia lanceolate, Pseudoalteromonas, Bacopa monniera, Ruscus aculeatus, Magnolia acuminata, Myrocarpus fastigiatus, Fraxinus szaboana, Gentiana rigescens, Garcinia cambogia, Taraxacum sinicum, Agave rigida, Citrus hystrix, Epimedium sagittatum, Zingiber officinale, Hedychium coronarium, Curcuma longa, Polygonatum cyrtonema, Bombyx mori, Dalbergia odorifera, Astragalus miler, Liquidambar styraciflua, Gynoma pentaphyllum, yeast, Sambucus nigra, Goodyera kwangtungensis, Dendrobium nobile, Cuscuta japonica, Chrysanthellum indicum, Phaseolus lunatus, Cibotium barometz, Spilanthes acmella, Lysimachia christinae, Pseudolarix kamepferi, Sarothamnus scoparius, Sciadopitys verticillata, Stephania cepharantha, Rosa laevigata, Calendula officinalis, Thuja occidentalis, Physalis alkekengi Franchetii, Malva sinensis, Ulex europaeus, Nepeta cataria, Schizonepeta tenuifolia, Pilea salwinensis, Murraya exotica, Allium tuberosum, Platycodon grandiflorum, Tanacetum vulgare, Chrysanthemum morifolium, Cichorium intybus, Polymnia sonchifolia, Dioscorea composita, Citrus reticulata, Equisetum giganteum, Sequoiadendron gigantea, Nymphaea gigantea, Macrocystis pyrifera, Lithothamnium calcarum, Pinus pentaphylla, Serenoa serrulata, Symphytum officinale, Selaginella tamariscina, Lilium tigrinum, Brassica oleracea capitata, Terminalia sericea, cassia Obtusifolia, Diospyros lotus, Kohhii ekisu, Abelmoschus esculentus, Hibiscus esculentus, Arnica chamissonis, Kunzea ericoides, Zingiber cassumunar, Piper methysticum, Dianthus caryophyllus, Theobroma cacao, Colax jugosus, Citrus clementina, Kluyveromyces, Laminaria cloustoni, Agarum cribosum, cuminum cyminum, Prunus amygdalus amara, Sophora angustifolia, Citrus aurantium amara, Momordica charantia, Fraxinus rhynchophylla, Picrasma quassioides, Carapa guaianensis, Citrus aurantium currassuviensis, Aloe barbadensis, Tinospora sinensis, Notopterygium forbesii, Lavandula intermedia, Tussilago farfara, fukitanpopo ekisu, Tussilago farfara, Scutellaria galericulata, Sasa quelpaertensis, Artemisia princeps, Ecklonia kurome, Chenopodium quinoa, Trichosanthes kirilowii, Tilia platyphyllos, Liriope muscari, Mahonia bealei, rahnellasoy, Cassia fistula, Myrica cerifera, Helichrysum bracteatum, Myrica cerifera, Mentha piperita, Cochlearia armoracia, Capsicum annuum, Polygonum hydro piper, Moringa oleifera, Citrus aurantifolia, Raphanus sotivus, Eucalyptus globulus, Lonicera caerulea, Terminalia catappa, Bidens tripartita, Geranium wilfordii, Omphalia lapidescens, Prunus salicina, Eclipta prostrata, Litchi chinensis, Forsythia suspensa, Nelumbium speciosum, Nelumbo nucifera, Cymbidium lianpan, Eperua falcata, Lansium domesticum, Mesona chinensis, Zanthoxylum nitidum, Sorghum bicolor, Hylocereus undatus, Aralia elata, Ligusticum jeholense, Anthyllis vulneraria, Polygonum tinctorium, Phellinus linteus, Ipomoea hederacea, Schizosaccharomyces, Cymbopogon schoenanthus, Lysimachia foenum-graecum, Campsis grandiflora, Hedera rhombea, Ocimum basilicum, Mentha spicata, Mentha viridis, Epilobium angustifolium, Cryptomeria japonica, Serissa serissoides, Gentiana scabra, Artemisia dracunculus, Agave americana, Bambusa vulgaris, Euphoria longan, Nephelium longana, Dimocarpus longan, Piper betle, Rhaponticum uniflorum, Phragmites communis, Aloe vera, Aloe matsu ekisu, Visnaga vera, Yucca aloifolia, Phragmites communis, Arundo donax, Artemia, Gossypium hirsutum, Pyrola calliantha, Liquidambar formosana, Plantago ovata, Adenophora retraphylla, Phalaenopsis lobbi, Apocynum venetum, Pikea robusta, Coffea robusta, Thujopsis dolabrata branch, Momordica grosvenori, podocarpus macrophyllus, ocimum Bosilicum, Balanites roxburghii, Raphanus sotivus, Metaplexis japonica, Trachelospermum jasminoides, Camellia kissii, Kalanchoe pinnata, Arachis hypogaea, Phaseolus mungo, Phaseolus radiatus, Vigna radiata, Melaleuca leucadendron viridiflora, Melaleuca viridiflora, Enantia chlorantha, Acacia decurrens, Amomum villosum xanthioides, Hieracium pilosella, Humulus japonicus, Gnetum parvifolium, Gentiana straminea, Quercus acutissima, Verbena officinalis, Dendrobium fimbriatum oculatum, Portulaca oleracea,

*Harungana madagascariensis, baphicacanthvs cusia, Romneya coulteri, Zantedeschia aethiopica, Pinus massoniana, Lantana camera, Lepidium meyenii, Ophiopogon japonicus, Elaeagnus glabra, Vitex trifolia, Cynanchum versicolor, Ona japonica, Lonicera caprifolium, Mangifera indica, Erodium stephanianum, Sapindus rarak, Siegesbeckia glabrescens, Solidago virgaurea, Terminalia bellerica, Coleus forskohlii, Plectranthus barbatus, Lonicera dasystyla, Chrysanthemum sinense, Cinchona pubescens, Phyllostachys nigra, Gouania javanica, Paulownia tomentosa, Verbascum thapsus, Mauritia flexuosa, Physalis pubescens, Lindera latifolia, Anona cherimolia, emmeisou ekisu, Corylus mendshurica, Atractyloides lancea, Melothria heterophylla, Rubus parvifolius, Hierochloe odorata, Commiphora myrrha, Cymbopogon martini, Sedum rosea, Rosa rugosa, rose petal, Aniba rosaeodora, Hibiscus sabdariffa, Epilobium roseum, Prunus mume, Monarda didyma, Carya illinoinensis, Orbignya speciosa, Acacia concinna, Ahnfeltia concinna, Actinidia deliciosa, Rubus deliciosus, Polygala senega, Sambucus canadensis, Campsis radicans, Corylus americana, Astragalus membranaceus mongholicus, Rosmarinus officinalis, Aglaia odorata, Krameria triandra, Myroxylon pereirae, Buddleja officinalis, Melicope hayesii, Polysiphonia lanosa, Taraktogenos kurzii, leuconostocradish, Changium smyrnioides, Astragalus membranaceus, Ormenis mixta, moroccan lava clay, Jasminum sambac, Eclipta prostrata, Fucus vesiculosus, Juniperus mexicana, Fouqueria splendens, Larrea mexicana, Dioscorea mexicana, Eugenia caryophyllata, Chamomillo recutita, Matricaria chamomilla, Paeonia suffruticosa, Vitex negundo cannabifolia, Momordica cochinchinensis, Hibiscus mutabilis; Chaenomeles sinensis, Oroxylum indicum, Hibiscus syriacus, Magnolia obovata, Indigofera tinctoria, Aloe arborescens, Astrocaryum murumuru, Bombax malabaricum, Limonia acidissima, Akebia quinata, Aucklandia lappa, Equisetum hiemale, Cuscuta australis, Harpagophytum procumbens, Durvillea antartica, Marsdenia condurango, Pfaffia paniculata, Artemisia abrotanum, Choerospondias axillaris, Schisandra sphenanthera, Sapindus emarginatus, Phyllostachys pubescens, endomyces, Arnebia guttata, Arabidopsis thaliana, Gellidiela acerosa, Lycium barborum, Citrus limon, Eucalyptus citriodora, Backhousia citriodora, Thymus citriodorus, Lippia citriodora, Cymbopogon citrates, Arctium lappa, Rhododendron chrysanthum, Rabdosia ternifolia, Achyranthes bidentata, Butyrospermum parkii (shea butter), Origanum vulgare, Opuntia streptacantha, Picea excelsa, Clematis apiifolia, Ligustrum lucidum, Solanum dulcamara, Thymus serpyllum, Juniperus communis, Salvia sclarea, Levisticum officinale, Syringa vulgaris, Glechoma hederacea, Malva sylvestris, Prunus humilis, Cystoseira tamariscifolia, Taraxacum officinale, Peucedanum ostruthium, Rubio tinctorum, Carum petroselinum, Petroselinum sativum, Achillea millefolium, Frangula alnus, Marrubium vulgare, Urtica urens, Nuphar luteum, Inula britannica, Primula vulgaris, Fraxinus excelsior, Xanthium strumarium, Pinus sylvestris, Ribes grossularia, Lapsana communis, Tilia cordata, Sorbus aucuparia, Abies alba, Prunus domestica, Castanea sativa, Dryopteris filix-mas, Agrimonia eupatoria, Larix europaea, Aesculus hippocastanum, Philadelphus coronarius, Populus tremuloides, Cypripedium pubescens, Lycopodium clavatum, Quercus sober, Fagus sylvatica, Isatis tinctoria, Prunus cerasus, Prunus avium, Berberis vulgaris, Brassica napus, Vaccinium myrtillus, Corylus avellana bud, Ascophyllum nodosum, Eupatorium fortunei, Curcuma phaeocaulis, Eriobotrya japonica, Terminalia bellerica, Humulus lupulus strobile, Saccharomyces cerevisiae, Plantago depressa, Psalliota campestris, Gaultheria procumbens, Malus domestica cell culture, Malus pumila, Pyrus malus, Rhamnus purshiana, Ficus religiose, Vitis vinifera, Clematis vitalba, Citrus paradisi, Taraxacum mongolicum, Syzygium jambos, Limonium vulgare, Tilia vulgaris, Pyrola decorata, Sargassum vulgare, Citrus medico vulgaris, Triticum aestivum, Aesculus chinensis, Paris polyphylla chinensis, Alnus firmifolia, Rhus vemiciflua, Thaumatococcus danielli, Copsella bursa-pastoris, Porphyra umbilicalis, Doemonorops draco, Epipremnum pinnatum, Sasa kurilensis, Lythrum salicaria, Acmella oleracea, Euryale ferox, Rubia cordifolia, Notopterygium incisum, Ecklonia cava, orchis mascula, Rosa multiflora, Polygonum fagopyrum, Solanum melongena, Apium graveolens, Gentiana macrophylla, Zanthoxylum piperitum, Prinsepia utilis, Bambusa tuldoides munro, Artemisia annua, Helwingia japonica, Vatica astrotricha, Bambusa textilis, Celosia argentea, Swertia mileensis, Dianthus superbus, Aspergillus ferment, Rhodiola sacra, Macadamia integrifolia, Polygonum bistorta, Undaria pinnatifida, Coleus barbatus, Panax ginseng, Moschus artifactus, Lonicera japonica, Lilium japonicum, Lotus japonicus symbiosome, Chamaecyparis obtusa, Cnidium officinale, Angelica japonica, Torreya nucifera, Coptis japonica, Castanea crenata, Chaenomeles japonica, Nuphar japonicum, Dioscorea japonica, Prunus lannesiana, Swertia japonica, Callicarpa japonica, Rubus villosus, Uncaria tomentosa, Terminalia chebula tomentella, Epimedium pubescens, Yucca filamentosa, Cystoseira amentacea, Caespitosa branchycarpa, Cistanche deserticola, Myristica fragrans, Cinnamomum cassia, Furcellaria lumbricalis, lactococcus ferment, Boswellia carterii, Thymus mastichina, Actinidia arguta, Prinsepia uniflora serrata, Crataegus oxyacantha, Saururus chinensis, Gleditsia triacanthos, Gentiana triflora, Sparganium stoloniferum, Viola tricolor, Bidens pilosa, Akebia trifoliata, Sapindus trifoliatus, Epimedium sagittatum, Larrea tridentata, Artemisia umbelliformis, Chimaphila umbellate, Morus alba, Taxillus chinensis, Leptospermum scoparium, Adenophora stricta, Ammopiptanthus mongolicus, Hippophae rhamnoides, Adenium obesum, Abronia villosa, Helichrysum arenarium, Barosma betulina, Camellia japonica, Artemisia montana, Litsea cubeba, Alpinia japonica, Arnica montana, Pyrus sorbus, Crataegus pinnatifida major, Scabiosa arvensis, Liriope spicata prolifera, Kaempferia galanga, Prunus davidiana, Ipomoea hungaiensis, Hyptis suaveolens, Dioscorea opposita, Lonicera confusa, Wasabia japonica, Cornus officinalis, Caulerpa taxifolia, Corallina officinalis, Paeonia lactiflora, Bergenia ligulata, Cnidium monnieri, Fragaria indica, Waltheria indica, Periostracum serpentis, Belamcanda chinensis, Thymus vulgaris, Rosa moschata, Lycopodium japonicum, Himanthalia elongata, Crambe abyssinica, Hyssopus officinalis, Orthosiphon stamineus, Cimicifuga foetida, Rhodiola sacra, Ocimum sanctum, Acarus tatarinowii, Ulva lactuca, asparagus officinalis, Lysionotus pauciforus, Gypsum fibrosum, Centipeda cunninghamii, Aleurites moluccanus bakoly, Punica granatum, Melaleuca ericifolia, Dianthus chinensis, Centaurea cyanus, Quisqualis indica, Diospyros kaki, Streptococcus thermophilus ferment, Thermus thermophillus ferment, Gymnema sylvestre, Nardostachys jatamansi, Polygonum multiflorum, Euterpe oleracea, Althaea officinalis, Althaea rosea, Salvia japonica, Salvia officinalis, Dioscorea batatas, Evernia furfuracea, Rhododendron arboreum, trichosanthes rosthornii, Mentha aquatica, Silybum marianum, Polygonum orientale, Pongamia pinnata, Aphanothece sacrum, Sisymbrium irio, Cardamine lyrata, Narcissus tazetta bulb, Typha angustifolia, Menyanthes trifoliata, Nymphaea tetragona, Withania somnifera, Luffa cylindrica,*

*Tricholoma matsutake, Armillaria matsutake, isatis indigotica, Cola acuminata, Cola acuminata, Liquidambar orientalis, Caesalpinia sappan, Jasminum officinale, Jasminum grandiflorum, Setaria italica, Citrus aurantium tachibana, Juniperus oxycedrus, Tamarindus indica, Physalis alkekengi, Polygonum capitatum, Ziziphus jujuba spinosa, Allium sativum, Cyathea medullaris, Vitex agnus castus, Fusanus spicatus, Lavandula spica, Cucurbita maxima, Shorea robusta resin, Amomum xanthioides, Cynomorium songaricum, Vanilla tahitensis, Gardenia tahitensis, Agave tequilana, Pseudostellaria heterophylla, Pueraria mirifica, Epiphyllum oxpetalum, Santalum album, Rheum tanguticum, Laminaria saccharina, Acer saccharum, Pinus lambertiana, Prunus persica, Rhodomyrtus tomentosa, Turnera diffusa, Ampelopsis cantoniensis grossedentata, Parabarium micranthum, Asparagus cochinchinensis, Lonicera macrantha, Semiaquilegia adoxoides, Gastrodia elata, Asparagus cochinchinensis, Asparagus lucidus, Magnolia sieboldii, Aesculus wilsonii, Prunus amygdalus dulcis protein, Beta vulgaris, Rubus suavissimus, Citrus aurantium dulcis, Citrus sinensis, Cucumis melo, Stevia rebaudiana, Eupatorium rebaudianum, Porphyra yezoensis, Gentiana manshurica, Murraya koenigii, Mesua ferrea, Dendrobium candidum, Adianturn capillus veneris, Pheretima vulgaris, Geranium thunbergii, Lespedeza capitata, Pelargonium capitatum, geranium, Phryma leptostachya, Speranskia tuberculata, Rosa damascena, Bolboma paniculatum, Eupolyphaga seu steleaphaga, Evolvulus alsinoides, Tulipa kaufmanniana, Smilax glabra, Ipomoea hungaiensis, Pseudolarix amabilis, Hypericum patulum, Inula helenium, Cuscuta chinensis, Pisum sativum, Polianthes tuberosa, Tagetes erecta, Vaccaria segetalis, Magnolia biondii, Pheretima guillelmi, Sargassum fulvellum, Micrococcus lysate, Sasa veitchii, Amaranthus caudates, Potentilla chinensis, Curcuma wenyujin, Citrus unshiu, Cydonia oblonga, Pyrus cydonia, Xanthoceras sorbifolia, Equisetum arvense, Lactuca sativa, Diospyros ebenum, Vigna aconitifolia, Lindero strychnifolia, Cuttlefish, Epimedium wushanense, Sempervivum tectorum, Sapindus mukurossi, Pongamia glabra, Brassica rapa, Evodia rutaecarpa, Sterculia plantifolia, Galla rhois gallnut, Coleus scutellarioides, Acanthopanax gracilistylus, Meconopsis quintuplinervia, Schizandra chinensis, Arctium majus, Magnolia sprengeri, Myosotis sylvatica, Salvia hispanica, Tillandsia usneoides, Abies sibirica, Larix sibirica, Yucca schidigera, Citrullus lanatus, Cucurbita pepo, Valeriana celtica, Rumex occidentalis, Panax quinquefolium, Sambucus nigra, Pyrus communis, Primula sikkimensis, Cinnamomum zeylanicum, Mourera fluviatilis, Siegesbeckia orientalis, Stachyurus himalaicus, Prunus serrulata, Mimosa tenuiflora, Euglena gracilis polysaccharide, Acorus gramineus, Mahonia fortunei, Leonurus sibiricus, Sphacelaria scoparia, Calanthe discolor, Shorea stenoptera butter, Bupleurum scorzonerifolium, Aframomum angustifolium, Cassia angustifolia, Artemisia dracunculus, Echinacea angustifolia, Vaccinium angustifolium, Prunella vulgaris, Tuber aestivum, Quercus robur, Satureia hortensis, Leucojum aestivum bulb, Agrimonia pilosa, Opuntia ficusindica, Geranium robertianum, Ampelopsis grossedentata, Aspalathus linearis, Siegesbeckia pubescens, Nigella glandulifera, Bergenia ciliata, Ferula foetida, Mentha suaveolens, Isodon japonicus, Citrus junos, Amomum aromaticum, Melissa officinalis, Cyperus rotundas, Iris florentina, Lentinus edodes mycelium, Vanilla planifolia, Zingiber aromaticus, viola odorata, Cymbopogon citratus, Prunus persica nectarina, Citrus aurantium bergamia, Mosla chinensis, Liatris odoratissima, Schisandra lancifloli, Dipteryx odorata, Rosa odorata, Nymphaea odorata, Myrtus communis, Lathyrus odoratus, Pelargonium graveolens, Pimenta acris, Lemon ekisu, Citrus medica limonum, Abies balsamea, Amyris balsamifera, Helianthus annuus, Evernia prunastri, Schinus terebinthifolius, Chrysanthemum parthenium, Freesia refracta, Elettaria cardamomum, Allium macroon, Broussonetia kazinoki, ouricury, Coffea arabica, Gleditsia australis, Combretum micranthum, Cirsium setosum, Cassia tora, Hypericum erectum, Spilanthes callimorpha, Triticum aestivum, Euphrasia officinalis, Capsicum frutescens, Clematis armandii, Arctium minus, Chlorella vulgaris albus, Yucca glauca, Rumex acetosella, Tagetes minuta, Sargassum fusiforme, Camellia meiocarpa, Euphorbia cerifera, Laminaria ochroleuca, Valeriana officinalis, Allium chinensis, Tinospora cordifolia, Ajuga turkestanica, Arnebia euchroma, Astrocaryum vulgare, Gigartina stellata, Cimicifuga dahurica, Rubus chamaemorus, Armeniaca vulgaris, Prunus armeniaca, Arctostaphylos uva ursi, Fraxinus stylosa, Hydrangea macrophylla, Sparassis crispa, Spiraea salicifolia, Rosa rubiginosa, paulownia imperialis, Usnea barbata, Cynanchum paniculatum, Hemerocallis fulva, Scrophularia ningpoensis, Sargassum filipendula, Heterotheca inuloides, Inula japonica, Citrus aurantium sinensis, Galanthus nivalis, Saussurea involucrata, Cedrus deodara, Sambucus adnata, Lavandula angustifolia, Salvia lavandulaefolia, Caviar, Albatrellus confluens, Corthellus shiitake, Acacia farnesiana, Commelina communis, bacillus ferment, Camelina sativa, Linum usitatissimum, Cymbopogon nardus, Betula platyphylla japonica, Opuntia coccinellifera, Nicotiana tabacum, Tofieldia japonica, Empetrum nigrum, Vetiveria zizanoides, Cistus ladaniferus, Ophiopogon bodinieri, Lathyrus palustris, Rhus semialata gall, Agropyron repens, Pinus pumilio, Alpinia speciosa, Avena sativa, Passiflora henryi, Baptisia tinctoria, Hizikia fusiforme, Codonopsis lanceolata, Averrhoa carambola, Thymus zygis, Hedera helix, Allium cepa, Calophyllum tacamahaca, Robinia pseudacacia, Pseudanabaena galeata, Echium lycopsis, Rosa centifolia, Potentilla erecta, Zizyphus joazeiro, Anacardium occidentale, Althaea officinalis, arutea ekisu, Salvia officinalis, Fomes officinalis, Rheum officinale, Polygonatum officinale, Veronica officinalis, Parietaria officinalis, Fumaria officinalis, tea-cocoyl hydrolyzed collagen, Cocos nucifera, Fragaria vesca, Glycine soja, Scoparia dulcis, Pueraria lobota, Juglans cathayensis, Daucus carota, Chrysanthemum indicum, Melastoma candidum, Rhus succedanea, Rosa multiflora, Crataegus cuneata, Mallotus japonicus, Dipsacus sylvestris, Nyctanthes arbor-tristis, Triticum monococcum, Platanus occidentalis, Solidago decurrens, Cananga odorata, mussel, Myrciaria dubia, Urtica dioica, Leonurus artemisia, Alpinia oxyphylla, Cassia italica, Brassica oleracea italica, Helichrysum italicum, Pinus pinea, Coix lacryma-jobi ma-yuen, Moringa pterygosperma, Artemisia capillaris, Stellaria dichotoma lanceolata, Tremella fuciformis, Acacia dealbata, Tilia tomentosa, Chloranthus japonicus, Ginkgo biloba, Epimedium brevicornum, Bambusa arundinacea, Azadirachta indica, Melia azadirachta, Commiphora mukul resin, Garcinia indica butter, Schleichera trijuga, Swertia chirata, Plukenetia volubilis, Prunus speciosa, Cerasus pseudocerasus, Prunus pseudocerasus, Viburnum prunifolium, Spartium junceum, Actinidia chinensis hispida, Cordyceps militaris, Brassica campestris, Camellia oleifera, Olea europaea, Cyperus esculentus, Pinus tabulaeformis, Elaeis guineensis, Amorphophallus campanulatus, Smilax utilis, Citrus grandis, Phyllanthus emblica, Houttuynia cordata, Spiraea ulmaria, Guazuma ulmifolia, Papaver rhoeas, Alchemilla vulgaris, Brassica oleracea acephala, Cycnoches cooperi, Hoematococcus pluvialis, Iris ensata, Pimento officinalis, Magnolia*

*denudata bud, Zea mays starch, Polygonatum odoratum, Tulipa gesneriana, Prunus japonica, Guaiacum officinale, Coriandrum sativum, Juniperus chinensis xylem, Citrus japonica, Citrus madurensis, Mentha rotundifolia, Angelica archangelica, Drosera rotundifolia, Ipomoea purpurea, Triticum vulgare turgidum, Gypsophila paniculata, Polygala tenuifolia, Laurus nobilis, Rosa chinensis, Oenothera biennis, Vaccinium vitis-idaea, Styrax tonkinensis resin, Saussurea lappa, Coptis teeta, Paris polyphylla yunnanensis, Rosa hybrid, Trametes versicolor, Lavandula hybrida, Hordeum distichon, Lansium domesticum, Ziziphus jujuba, Gleditsia sinensis, Quillaja saponaria, Lycopus lucidus hirtus, Alisma orientale, Pistacia lentiscus, Premna fulva, swertia bimaculata, Cinnamomum camphora, Prunus pedunculata, Prunella asiatica, Ceratonia siliqua, Epimedium Grandiflorum, Dictyophora indusiata, Dioscorea villosa, Narcissus jonquilla, Corchorus olitorius, Poterium officinale, Kappaphycus alvarezii, Sanguisorba officinalis longifolia, Pinus palustris, Rheum palmatum, Palmaria palmato, Laminaria digitata, Rhodymenia palmata, Glycyrrhiza inflata, Conarium commune, Aesculus chinensis chekiangensis, Corylus heterophylla, Sesamum indicum, Eruca sativa, Anemarrhena asphodeloides, Gardenia florida, Gardenia jasminoides, Gardenia jasminoides, Ona sessilifolia, Fragaria chiloensis, Gevuina avellana, Rehmannia chinensis, Stachyurus chinensis, Ganoderma sinensis, Actinidia chinensis, Skeletonema costatum, Artemisia absinthium, Angelica pubescens, Chondrus crispus, Magnolia kobus, Rumex crispus, Calluna vulgaris, Halopteris scoparia, Cordyline terminalis, Hibiscus rosa-sinensis, Cyanotis arachnoidea, Polyporus umbellatus, Bamboo vinegar, Panax japonicus, Bamboo charcoal, Phyllostachys pubescens, Zanthoxylum alatum, Catalpa ovata, Lithospermum erythrorhizon, Syringa oblata, Petasites hybridus, Viola yedoensis, Chrysanthemum zawadskii, Peucedanum decursivurn, Bletia hyacinthina bulb, Mirabilis jalapa, Medicago sativa, Porphyridium cruenturn, Echinacea purpurea, Perilla frutescens, Pterocarpus santalinus, Wisteria sinensis, Lagerstroemia indica, Magnolia liliflora, Aster tataricus, Astragalus sinicus, Ganoderma sinensis, Alkanna tinctoria, Elaeis guineensis, Trachycarpus fortunei, Asparagus racemosus,* and *Cimicifuga racemosa.*

In the case where the biological material is a plant, the extraction may be performed using the entire plant or one or more parts of the plant, and notably chosen from the root, the stalk, the bark, the flower, the seed, the germ and/or the leaf, and mixtures thereof. According to an advantageous embodiment, it is preferentially the aerial parts, i.e. the leaves and the stalks, and preferentially the leaves.

In a particular embodiment, the biological material is the olive tree, in particular olive tree leaves, orange, in particular orange fruit peel, common verbena, in particular its leafy stalks, or candle bush (*Cassia alata*), in particular its leaves.

Extractable Compounds

A variety of compounds or substances may be extracted using coconut water as extraction solvent. The extractable compounds according to the present invention include, in a nonexhaustive manner, terpenes, terpenoids, flavones and flavonoids, steroids, sterols, saponins and sapogenins, alkanes, alkaloids, amines, amino acids, aldehydes, iridoids, phenylpropanoids, alcohols, polyols, lipids, fatty acids, lignans, phenols, pyrones, butenolides, lactones, chalcones, ketones, benzenes, cyclohexanes, glucosides, glycosides, cyanidines, furans, phorbols, quinones and phloroglucinols in aglycone form or, where appropriate, in glycosyl form. The invention may also be applied to the extraction of bioactive molecules of high molecular mass such as proteins, peptides, enzymes, polysaccharides, oligosaccharides and carbohydrates.

By way of example, the extractable compounds according to the present invention include, in a nonexhaustive manner, the following substances: catechin, epicatechin, catechin gallate, epicatechin gallate, gallocatechin, epigallocatechin, gallocatechin gallate, epigallocatechin gallate, catechic tannins, gallic tannins, rhamnetin, fisetin, robinetin, gossypetin, orientin, homoorientin, cirsiliol, homoprotocatechic acid, dihydrocaffeic acid, ethyl ester of protocatechic acid, propyl gallate, gallic acid, protocatechic acid, caffeic acid, rosmarinic acid, esculetin, 4-methylesculetin, nordalbergin, chlorogenic acid, phenethyl ester of caffeic acid, chicoric acid, echinacoside, beta-D-glucopyranoside, verbascoside, hydroxytyrosol, maclurin, 3,4-dihydroxybenzaldehyde, 3,4-dihydroxybenzophenone, butein, 3,4-dihydroxyacetophenone, marein, eriodictyolchalcone, pyrocatechol, nordihydroguaiaretic acid, 3-hydroxydaidzein, oleuropein, maritimein, salicylic acid, myristicin, eugenol, umbelliferone, esculetin, juglone, resveratrol, kaempferol, afzelin, astragalin, juglanin, robinin, trifolin, kaempferol-3-O-rutinoside, daidzin, puerarin, procyanidines, dalphiniol, herniarin, skimmin; marmarin, marmesin, angelicin, imperatorin, xanthotoxin, bergapten, psoralen, linalool, 1,8-cineole, alpha-pinene, beta-sitosterol, campestrol, stigmasterol, fruit acids (lactic acid, glycolic acid, malic acid, citric acid, etc.), vitamin E (tocopherols), vitamin A (retinoids), provitamin A (carotenoids), vitamin C, B vitamins (thiamin, biotin, nicotinamide, pantothenic acid, etc.), camphor, menthol, myrcene, abyssinone I, abyssinone V, afzelechin, ampelopsin, aromadendrin, auriculoside, broussin, broussonin C, butin, butrin, davidigenin, diffutin, 7,4'-dihydroxyflavan, 2,6-dihydroxy-4'-methoxydihydrochalcone, 7,3'-dihydroxy-4-methoxy-8-methylflavan, 7,4'-dihydroxy-8-methylflavan, 6,8-diprenylnaringenin, dracorubin, eriocitrin, eriodictyol, farrerol, fisetinidol, fisetinidol-4-ol, fustin, garbanzol, glabranin, glepidotin B, glycyphyllin, hesperetin, hesperidin, homoeriodictyol, 7-hydroxyflavan, isochamaejasmin, isosakuranetin, isouriaretin, kolaflavanone, liquiretigenin, manniflavanone, 6-methoxytaxifolin, narirutin, neoastilbin, neoeriocitrin, neohesperidin, phloretin, phellamurin, phloridzin, pinobanksin, pinocembrin, pinocembrin 7-rhamnosyl glucoside, piperaduncin B, poncirin, prenylnaringenin, sakuranetin, silandrin, silybin, silychristin, sophoranone, strobopinin, taxifolin, taxifolin 3-O-acetate, tephrowatsin, theasinensin A, uvaretin, naringenin, naringenin glycosides, o-glucosylrutin, α-glucosylmyricetin, α-glucosylisoquercetin, α-glucosylquercetin, dihydroquercetin (taxifolin), hesperidin (3',5,7-trihydroxy-4'-methoxyflavanone 7-rhamnoglucoside, hesperitin 7-O-rhamnoglucoside), neohesperidin, rutin (3,3',4',5,7-pentahydroxyflavone 3-rhamnoglucoside, quercetin 3-rhamnoglucoside), diosmin (3',4',7-trihydroxy-5-methoxyflavanone 7-rhamnoglucoside), eriodictin, apigenin 7-glucoside (4',5,7-trihydroxyflavone 7-glucoside), kaempferol, quercitrin, avicularin, myricitin.

Extracts and Uses

The extract obtained via the process and the uses thereof constitute one of the subjects of the present invention.

In one embodiment, the extract is characterized by the presence of coconut water. Thus, the extract is obtained via the extraction method according to the present invention, without a step of removing the coconut water, notably without a step of purification or fractionation.

Thus, the invention is also directed toward the use of said extract for the manufacture of a nutraceutical composition, of a dietetic or dietary product, of a nutritional supplement, of a pharmaceutical composition, notably a dermatological composition, or of a cosmetic composition. The invention also relates to a nutraceutical composition, a dietetic or dietary product, a nutritional supplement, a pharmaceutical composition, notably a dermatological composition, or a cosmetic composition comprising an extract obtained via the process according to the present invention.

The invention also relates to a method for preparing a nutraceutical, dietetic, dietary, nutritional, pharmaceutical, notably dermatological, or cosmetic composition, comprising the preparation of an extract of plant, animal and/or prokaryotic biological material according to the method according to the present invention and the incorporation of the extract thus obtained into a nutraceutical, dietetic, dietary, nutritional, pharmaceutical, notably dermatological, or cosmetic composition. Advantageously, the composition thus obtained contains coconut water which has served as extraction solvent for the extract.

The extract according to the invention is thus orally and topically acceptable.

The extract obtained according to the invention is preferentially present in the cosmetic, nutraceutical and/or pharmaceutical, in particular dermatological, composition in a concentration of from $1\times10^{-4}$% to 10% by weight, preferentially between $1\times10^{-4}$% and 5% by weight, even more advantageously between $1\times10^{-3}$% and 3% by weight, relative to the total weight of the composition, in particular between 0.001 and 0.1% by weight relative to the total weight of the composition.

The cosmetic, nutraceutical or pharmaceutical, preferentially dermatological, compositions according to the invention may contain any suitable solvent and/or any suitable cosmetic, nutraceutical or pharmaceutical, preferentially dermatological, vehicle and/or any suitable excipient, optionally in combination with other compounds of interest. The terms "suitable cosmetic, nutraceutical, pharmaceutical or dermatological vehicle" used herein mean that the composition or the components thereof are suitable for use in contact with human skin or orally without any undue toxicity, incompatibility, instability, allergic response, or equivalents thereof.

Advantageously, the compositions according to the invention are formulated in a form chosen from the group consisting of an aqueous or oily solution, a cream, an aqueous gel or an oily gel, notably in a jar or tube, notably a shower gel, a shampoo; a milk; an emulsion, a microemulsion or a nanoemulsion, notably oil-in-water or water-in-oil or multiple or silicone-based emulsion; a lotion, notably in a glass or plastic bottle or measuring bottle or aerosol bottle; a vial; a liquid soap; a dermatological bar; an ointment; a mousse; an anhydrous product, which is preferably liquid, pasty or solid, for example in stick form; powders.

The cosmetic compositions according to the invention may be applied topically, to a surface of the body chosen from facial and/or bodily skin where the cosmetic property of the extract obtained is desirable, for example to an uncomfortable, unesthetic and/or unpleasant region of the body, such as the forehead, the cheeks and/or the chin, areas of the body such as the scalp, the arms, the hands, the legs, the tummy and/or the chest.

For the compositions according to the invention, the excipient contains, for example, at least one compound chosen from the group consisting of preserving agents, emollients, emulsifiers, surfactants, moisturizers, thickeners, conditioning agents, matt-effect agents, stabilizers, antioxidants, texturing agents, sheen agents, film-forming agents, solubilizers, pigments, dyes, fragrances and sunscreens.

These excipients are preferably chosen from the group consisting of amino acids and derivatives thereof, polyglycerols, esters, cellulose polymers and derivatives, lanolin derivatives, phospholipids, lactoferrins, lactoperoxidases, sucrose-based stabilizers, vitamin E and derivatives thereof, natural and synthetic waxes, plant oils, triglycerides, unsaponifiable substances, phytosterols, plant esters, silicones and derivatives thereof, protein hydrolyzates, jojoba oil and derivatives thereof, liposoluble/water-soluble esters, betaines, amine oxides, plant extracts, saccharose esters, titanium dioxides, glycines and parabens, and even more preferably from the group consisting of butylene glycol, steareth-2, steareth-21, glycol-15 stearyl ether, cetearyl alcohol, phenoxyethanol, methylparaben, ethylparaben, propylparaben, butylparaben, butylene glycol, natural tocopherols, glycerin, sodium dihydroxycetyl phosphate, isopropyl hydroxycetyl ether, glycol stearate, triisononanoin, octyl cocoate, polyacrylamide, isoparaffin, laureth-7, a carbomer, propylene glycol, glycerol, bisabolol, a dimethicone, sodium hydroxide, PEG 30-dipolyhydroxystearate, capric/caprylic triglycerides, cetearyl octanoate, dibutyl adipate, grapeseed oil, jojoba oil, magnesium sulfate, EDTA, a cyclomethicone, xanthan gum, citric acid, sodium lauryl sulfate, mineral oils and waxes, isostearyl isostearate, propylene glycol dipelargonate, propylene glycol isostearate, PEG 8, beeswax, hydrogenated palm kernel oil glycerides, hydrogenated palm oil glycerides, lanolin oil, sesame oil, cetyl lactate, lanolin alcohol, castor oil, titanium dioxide, lactose, sucrose, low-density polyethylene, an isotonic saline solution.

Many cosmetically active ingredients known to those skilled in the art for improving the health and/or the physical appearance of the skin may be contained in the cosmetic compositions. A person skilled in the art knows how to formulate cosmetic or dermatological compositions to obtain the best effects. Moreover, the compounds described in the present invention may have a synergistic effect when they are combined with each other. These combinations are also covered by the present invention. The CTFA Cosmetic Ingredient Handbook, Second Edition (1992) describes different cosmetic and pharmaceutical ingredients commonly used in the cosmetics and pharmaceutical industry, which are suitable in particular for topical use. Examples of these classes of ingredients comprise, without being limited thereto, the following compounds: abrasives, absorbents, compounds for esthetic purposes such as fragrances, pigments, dyes, essential oils, astringents, etc. (for example: oil of clove, menthol, camphor, eucalyptus oil, eugenol, menthyl lactate, witch hazel distillate), antiacne agents, antiflocculant agents, antifoam agents, antimicrobial agents (for example: iodopropyl butyl carbamate), antioxidants, binders, biological additives, buffer agents, swelling agents, chelating agents, additives, biocidal agents, denaturing agents, thickeners, and vitamins, and derivatives or equivalents thereof, film-forming materials, polymers, opacifiers, pH regulators, reducing agents, depigmenting or lightening agents (for example: hydroquinone, kojic acid, ascorbic acid, magnesium ascorbyl phosphate, ascorbyl glucosamine), conditioning agents (for example: humectants).

Other aims, features and advantages of the invention will emerge clearly to a person skilled in the art on reading the explanatory description, which makes reference to examples that are given purely as illustrations and shall not in any way limit the scope of the invention.

The examples form an integral part of the present invention, and any feature appearing to be novel over any prior art whatsoever, from the description taken in its entirety, including the examples, forms an integral part of the invention in its function and in its general nature. Thus, each example has a general scope.

Moreover, in the examples, all the percentages are given on a weight basis, unless otherwise indicated, the temperature is expressed in degrees Celsius, unless otherwise indicated, and the pressure is atmospheric pressure, unless otherwise indicated.

EXAMPLES

Example 1

Effect of Various Waters of Constitution on the Extraction of Total Polyphenols from Olive Leaves and from Orange Fruit Peel

Example 1-1

Plant Waters

Several natural plant waters were tested.
Carrot and Lettuce Waters of Constitution Carrot and lettuce waters were extracted using the microwave hydrodiffusion and gravity (MHG) technique. This technique, which combines both heating with microwaves and gravity, has the advantage of being able to be transposed to the industrial scale. This technique is notably described in patent EP1955749 B1. This extraction is performed without solvent. The action of the microwaves heats the matrix until the cells burst. Thus, the cell contents, including the metabolites, are released and entrained with the intrinsic water by hydrodiffusion. The vapor formed condenses and gravity allows the extract to descend in the condenser. The water of constitution is then collected.

The conditions for extracting the carrot waters and the lettuce water by MHG were optimized and established at 20 minutes with a power of 1 W/g (with a maximum of 300 W).

The other two plant fluids tested (coconut water and *Aloe vera* juice) were purchased commercially. Three coconut waters of different origin were tested: coconut water A, coconut water B and coconut water C according to examples 1, 2, 3 and 4.

Example 1-2

Extraction of Polyphenols from Olive Leaves

Dried and ground olive (*Olea europaea* L.) leaves were extracted for 1 hour at 60° C. (plant/solvent ratio=1/10) in water and in each of the waters of constitution studied.

After cooling, centrifugation and filtration at 0.45 μm through PTFE filters, the total polyphenols were assayed in the extracts via the Folin-Ciocalteu method by UV-Vis spectrometry using oleuropein as calibration molecule.

The results expressed in mg of oleuropein/g of solids are presented in table I.

The extractions were performed in triplicate and the results represent the mean of the values determined.

TABLE I

Comparison of distilled water and of the waters of constitution as solvent for the extraction of the total polyphenols of olive leaves

| Extraction solvent | Total polyphenols (mg of oleuropein/g of solids) | Variation relative to the aqueous extract |
|---|---|---|
| Distilled water | 14.6 | — |
| Lettuce water | 12.7 | −13% |
| Carrot water | 11.5 | −21% |
| Coconut water A | 29.4 | +101% |
| Aloe vera water | 12.5 | −14% |

These results show that, surprisingly and unexpectedly, the use of coconut water as extraction solvent makes it possible to extract more total polyphenols from the olive leaves relative to water alone.

Example 1-3

Extraction of Polyphenols from Orange Peel

Dried and ground orange (*Citrus aurantium* L.) fruit peels were extracted and treated under the same conditions as the olive leaves of example 1.

The total polyphenols were assayed in the extracts via the Folin-Ciocalteu method by UV-Vis spectrometry using naringin as calibration molecule.

The results expressed in mg of naringin/g of solids are presented in table II.

The extractions were performed in triplicate and the results represent the mean of the values determined.

TABLE II

Comparison of distilled water and of the waters of constitution as solvent for the extraction of the total polyphenols of orange fruit peel

| Solvents | Total polyphenols (mg of naringin/g of solids) | Variation relative to the aqueous extract |
|---|---|---|
| Distilled water | 64.8 | — |
| Lettuce water | 74.0 | +14% |
| Carrot water | 65.5 | +1% |
| Coconut water A | 86.1 | +33% |

These results show that, as in the case of the olive leaves, the use of coconut water as extraction solvent makes it possible to extract more total polyphenols from the orange fruit peels relative to water alone.

These studies thus show that, among the natural plant waters tested, coconut water makes it possible to extract more total polyphenols relative to water alone.

Example 2

Effect of Coconut Water on the Extraction of Phytochemical Markers from Various Plant Matrices

Example 2-1

Extraction of Oleuropein from Olive Leaves

Dried and ground olive leaves were added (plant/solvent ratio=1/10) with stirring to the extraction solvent (water, coconut waters), the pH of which was adjusted to 3 or to 4, for 1 hour at 80° C. The container serving for the extraction was closed (stopper or aluminum foil) to prevent evaporation of the solvent.

After cooling, centrifugation and filtration at 0.45 μm, the concentration of oleuropein in the liquid extracts was estimated directly by HPLC analysis.

The results expressed in mg of oleuropein/liter of extract are presented in table III.

The extractions were performed in triplicate and the results represent the mean of the values determined.

TABLE III

Comparison of distilled water and of coconut water as extraction solvent for oleuropein

| | pH3 | | pH4 | |
|---|---|---|---|---|
| Solvents | [oleuropein] in mg/L | Variation relative to the aqueous extract | [oleuropein] in mg/L | Variation relative to the aqueous extract |
| Distilled water | 234.5 | — | 203.0 | — |
| Coconut water B | 322.5 | +37.5% | 275.5 | +35.7% |

Example 2-2

Extraction of Naringin from Orange Fruit Peels

Dried and ground orange fruit peels were added (plant/solvent ratio=1/10) with stirring to the extraction solvent (water, coconut water), the pH of which was adjusted to 3 or to 4, for 1 hour at 80° C. in a closed medium to prevent evaporation of the solvent.

After cooling, centrifugation and filtration at 0.45 μm, the concentration of naringin in the liquid extracts was estimated directly by HPLC analysis.

The results expressed in mg of naringin/liter of extract are presented in table IV.

The extractions were performed in triplicate and the results represent the mean of the values determined.

TABLE IV

Comparison of distilled water and of coconut water as extraction solvent for naringin

| | pH3 | | pH4 | |
|---|---|---|---|---|
| Solvents | [naringin] in mg/L | Variation relative to the aqueous extract | [naringin] in mg/L | Variation relative to the aqueous extract |
| Distilled water | 50.5 | — | 58.0 | — |
| Coconut water B | 106.5 | +110.9% | 94.5 | +62.9% |

Example 3

Extraction of Verbascoside from Leafy Stalks of Common Verbena

Dried and ground leafy stalks of common verbena (*Verbena officinalis* L) were added (plant/solvent ratio=1/10) with stirring to the extraction solvent (water, coconut water), the pH of which was adjusted to 3 or to 4, for 1 hour at 80° C. in a closed medium to prevent evaporation of the solvent.

After cooling, centrifugation and filtration at 0.45 μm, the concentration of verbascoside in the liquid extracts was estimated directly by HPLC analysis.

The results expressed in mg of verbascoside/liter of extract are presented in table V.

The extractions were performed in triplicate and the results represent the mean of the values determined.

TABLE V

Comparison of distilled water and of coconut water as extraction solvent for verbascoside

| | pH3 | | pH4 | |
|---|---|---|---|---|
| Solvents | [verbascoside] in mg/L | Variation relative to the aqueous extract | [verbascoside] in mg/L | Variation relative to the aqueous extract |
| Water | 917 | | 696 | |
| Coconut water A | 1031 | +12.4% | 1063 | +52.7% |
| Coconut water B | 1077 | +17.4% | 1174 | +68.7% |

Example 4

Extraction of Kaempferol 3-O-Sophoroside from *Cassia alata* Leaves

Dried and ground *Cassia alata* L. leaves were added (plant/solvent ratio=1/10) with stirring to the extraction solvent (water, coconut water), the pH of which was adjusted to 3 or to 4, for 1 hour at 80° C. in a closed medium to prevent evaporation of the solvent.

After cooling, centrifugation and filtration at 0.45 μm, the concentration of kaempferol 3-O-sophoroside (K3OS) in the liquid extracts was estimated directly by HPLC analysis.

The results expressed in mg of K3OS/liter of extract are presented in table VI.

The extractions were performed in triplicate and the results represent the mean of the values determined.

TABLE VI

Comparison of distilled water and of coconut water as extraction solvent for kaempferol 3-O-sophoroside

| | pH3 | | pH4 | |
|---|---|---|---|---|
| Solvents | [K3OS] in mg/L | Variation relative to the aqueous extract (%) | [K3OS] in mg/L | Variation relative to the aqueous extract (%) |
| 80:20 EtOH/water | 1890 | | | |
| Water | 1180 | | 1140 | |
| Coconut water A | 1360 | 15 | 1320 | 16 |
| Coconut water B | 1440 | 22 | 1420 | 25 |

The results obtained show that coconut water, irrespective of its origin and the pH studied, makes it possible to extract the target compounds in a higher concentration relative to distilled water alone.

Example 5

Extraction with Coconut Water Under Subcritical Conditions

These tests were performed with a commercial coconut water C.

10 g of ground orange fruit peels were introduced into a tea filter which was placed in a reactor with 100 ml of solvent (water or coconut water). The extraction was performed by means of an UltraClave microwave reactor (Milestone). The oxygen was removed by introducing nitrogen which serves to place the reactor under pressure. The extractions were performed at a pressure of 30 bar, for 10 minutes and at various temperatures. At the end of the extractions, the medium was filtered and then analyzed.

The total polyphenols are assayed in the extracts via the Folin-Ciocalteu method by UV-Vis spectrometry using naringin as calibration molecule. The results expressed in mg of naringin/g of solids are presented in table VII.

TABLE VII

Comparison of distilled water and of coconut water under subcritical conditions as solvents for extracting naringin from orange fruit peels

| Temperature | Total polyphenols (mg of naringin/g of solids) | | Variation relative to water (%) |
| --- | --- | --- | --- |
| | Water | Coconut water C | |
| 105° C. | 31.0 | 37.1 | +19.7% |
| 115° C. | 21.2 | 40.2 | +89.6% |
| 125° C. | 23.8 | 51.2 | +115.1% |

The results obtained show that coconut water makes it possible to extract the polyphenols in a higher concentration relative to distilled water alone. In addition, with distilled water, browning of the extracts is observed, which is not observed with the coconut water.

The invention claimed is:

1. A method for preparing an extract from a plant, animal and/or prokaryotic biological material, comprising incubating said plant, animal and/or prokaryotic biological material with a coconut water, and recovering said extract.

2. The method of claim 1, wherein the coconut water and the plant, animal and/or prokaryotic biological material are present in a weight ratio of between 2:1 and 100:1 for preparing the extract.

3. The method of claim 1, wherein the coconut water and the plant, animal and/or prokaryotic biological material are present in a weight ratio of 10:1 for preparing the extract.

4. The method of claim 1, wherein an anionic, cationic or nonionic surfactant is added to the coconut water to facilitate the extraction of the extract and/or compounds therein.

5. The method of claim 1, wherein the extraction step is performed at a temperature of between 2° C. and 100° C.

6. The method of claim 1, wherein the extraction step is performed under subcritical conditions.

7. The method of claim 6, wherein the extraction is performed under nitrogen and under greater than atmospheric pressure and at a temperature of between 100 and 140° C. for 5 minutes to 1 hour.

8. The method of claim 1, wherein the extraction step is assisted by microwaves or ultrasound.

9. The method of claim 1, wherein the biological material consists of a plant or one or more parts thereof.

10. A method for preparing a nutraceutical, dietetic, dietary, nutritional, pharmaceutical, dermatological, or cosmetic composition, comprising preparing an extract of plant, animal and/or prokaryotic biological material according to the method of claim 1, and incorporating said extract into a nutraceutical, dietetic, dietary, nutritional, pharmaceutical, dermatological, or cosmetic composition.

11. The method of claim 1, further comprising recovering at least one compound from the extract.

12. The method of claim 11, comprising immersing said plant, animal and/or prokaryotic biological material in the coconut water, extracting a mixture obtained, and recovering the at least one compound using purification step selected from one or more of centrifugation, filtration, evaporation, concentration, and fractionation.

13. The method of claim 11, wherein the at least one compound is selected from at least one terpene, at least one terpenoid, at least one flavone, at least one flavonoid, at least one steroid, at least one sterol, at least one saponin, at least one sapogenin, at least one alkane, at least one alkaloid, at least one amine, at least one amino acid, at least one aldehyde, at least one iridoid, at least one phenylpropanoid, at least one alcohol, at least one polyol, at least one lipid, at least one fatty acid, at least one lignan, at least one phenol, at least one pyrone, at least one butenolide, at least one lactone, at least one chalcone, at least one ketone, at least one benzene, at least one cyclohexane, at least one glucoside, at least one glycoside, at least one cyanidine, at least one furan, at least one phorbol, at least one quinone, at least one phloroglucinolsin aglycone form or in glycosyl form, at least one bioactive molecule, and mixtures thereof.

14. The method of claim 13, wherein the at least one compound comprises at least one bioactive molecule selected from at least one protein, at least one peptide, at least one enzyme, at least one polysaccharide, at least one oligosaccharide, at least one carbohydrate, and mixtures thereof.

15. The method of claim 1, wherein the coconut water and the plant, animal and/or prokaryotic biological material are present in a weight ratio of between 1:1 and 100:1 for preparing the extract.

16. The method of claim 1, wherein the coconut water and the plant, animal and/or prokaryotic biological material are present in a weight ratio of between 5:1 and 20:1 for preparing the extract.

17. The method of claim 1, wherein the extraction step is performed at a temperature of between 20° C. and 90° C.

18. The method of claim 1, wherein the extraction step is performed at a temperature of between 50° C. and 80° C.

19. The method of claim 1, wherein the extraction step is performed for 30 minutes to 1 day.

20. The method of claim 1, wherein the extraction step is performed for 1 to 3 hours.

* * * * *